United States Patent
Nardi et al.

(10) Patent No.: US 9,599,498 B2
(45) Date of Patent: Mar. 21, 2017

(54) METHOD FOR DETERMINING THE DENSITY OF A MULTIPHASE FLUID, DENSITOMETER USING SAID METHOD AND MULTIPHASE METER USING SAID DENSITOMETER

(75) Inventors: Paolo Aditeo Nardi, Milan (IT); Paolo Calciolari, Lonigo (IT); Stefano Bernardi, Padua (IT)

(73) Assignee: PIETRO FIORENTINI SPA, Arcugnano (IT)

( * ) Notice: Subject to any disclaimer, the term of this patent is extended or adjusted under 35 U.S.C. 154(b) by 1149 days.

(21) Appl. No.: 13/264,958

(22) PCT Filed: Apr. 28, 2011

(86) PCT No.: PCT/EP2011/056799
§ 371 (c)(1),
(2), (4) Date: Dec. 9, 2011

(87) PCT Pub. No.: WO2011/117426
PCT Pub. Date: Sep. 29, 2011

(65) Prior Publication Data
US 2013/0035879 A1  Feb. 7, 2013

(30) Foreign Application Priority Data

Apr. 29, 2010 (IT) .................................. VI10A0117

(51) Int. Cl.
*G01F 1/74* (2006.01)
*G01N 9/24* (2006.01)
(Continued)

(52) U.S. Cl.
CPC ................ *G01F 1/74* (2013.01); *G01N 9/24* (2013.01); *G01N 9/36* (2013.01); *G01N 33/2823* (2013.01)

(58) Field of Classification Search
CPC ... G01F 1/74; G01N 9/24; G01N 9/36; G01N 33/2823; G01N 33/28
(Continued)

(56) References Cited

U.S. PATENT DOCUMENTS

| 5,003,502 A | 3/1991 | Davis |
| 5,486,695 A * | 1/1996 | Schultz ................. E21B 47/082 |
| | | 250/254 |

(Continued)

FOREIGN PATENT DOCUMENTS

| FR | 2582095 A1 | 11/1986 |
| GB | 2210461 A | 6/1989 |

(Continued)

*Primary Examiner* — Gregory J Toatley
*Assistant Examiner* — Terence Stifter, Jr.
(74) *Attorney, Agent, or Firm* — IP Strategies (57) ABSTRACT

Method for determining the density (D) of a multiphase fluid (F) flowing through a pipe (1) and containing a gas (G) which determines a fluctuation of the actual instantaneous density of the fluid (F), said method comprising the following steps: defining a series of consecutive time periods (S0, S) which are shorter than the time length corresponding to the highest frequency-component of the fluctuation of the actual instantaneous density; conveying through a section (2) of the pipe (1) a photon beam (3) suited to undergo an attenuation while crossing the fluid (F); counting the actual number (A) of photons of the beam (3) which cross the pipe (1) during a first time period (S) of the series; calculating a corrected count (C) as the weighted average value of the actual count (A) and of the corrected count (C0) calculated for the preceding time period (S0); converting the value of the corrected count (C) into a corresponding value of the density (D) of the multiphase fluid (F) for the first time period (S) through a predefined function.

22 Claims, 5 Drawing Sheets

(51) Int. Cl.
*G01N 9/36* (2006.01)
*G01N 33/28* (2006.01)

(58) Field of Classification Search
USPC .......................................... 702/50
See application file for complete search history.

(56) References Cited

U.S. PATENT DOCUMENTS

| | | | |
|---|---|---|---|
| 7,081,616 B2* | 7/2006 | Grau | G01V 5/101 |
| | | | 250/253 |
| 2008/0112536 A1* | 5/2008 | Kulik | G01N 9/24 |
| | | | 378/89 |
| 2009/0296084 A1* | 12/2009 | Odom | G01V 5/12 |
| | | | 356/317 |
| 2010/0164514 A1* | 7/2010 | Brandt | G01F 1/74 |
| | | | 324/694 |

FOREIGN PATENT DOCUMENTS

| | | |
|---|---|---|
| GB | 2390683 A | 1/2004 |
| WO | 2008150180 A2 | 12/2008 |

* cited by examiner

METHOD FOR DETERMINING THE DENSITY OF A MULTIPHASE FLUID, DENSITOMETER USING SAID METHOD AND MULTIPHASE METER USING SAID DENSITOMETER

FIELD OF THE INVENTION

The present invention concerns a method for determining the density of a mixture flowing through a pipe, particularly of a mixture comprising a liquid phase and a gaseous phase.

The present invention also concerns a densitometer using said method, and a multiphase meter including such densitometer.

BACKGROUND OF THE INVENTION

The method, the densitometer and the multiphase meter of the invention are particularly suited to be used in the oil extraction sector.

It is known that the fluid produced from an oil-well is a mixture of oil, water and gas, therefore known in the technical jargon as a "multiphase fluid".

In this field, it is required to determine the flow rate of the produced oil as accurately as possible, in order to quantify the actual profitability of the oil-well. The above determination is made by means of instruments commonly known as "multiphase meters", suitable to determine the flow rate of the multiphase fluid and the oil fraction contained in it.

As regards in particular the oil fraction, this is calculated by means of known formulas as a function of the gas volume fraction in the fluid (GVF) and of the fraction of water in relation to the total liquid phase in the fluid, known as "water-cut" (WC).

It is evident that, in order to determine said two quantities, it is necessary to measure two mutually independent physical properties of the fluid.

The above mentioned physical properties must be measured as accurately as possible, in order to avoid that any measurement errors, propagating to the calculated oil flow rate, make said calculation unreliable.

According to a known technique, which is described for example in the International Patent application WO90/02941 by CHR. MICHELSENS INSTITUTT, the dielectric permittivity and the density of the fluid are measured, from which it is possible to obtain the gas fraction and the water-cut by means of known correlation equations.

Generally, density is measured by means of a penetrant photon beam, normally of the gamma type, conveyed through the pipe at the level of a measurement section.

The fluid partially absorbs the photons, thus determining an attenuation of the beam whose entity depends on the fluid density.

The number of photons passing through the pipe during a predetermined time period, named the "sampling period", is counted, and divided by the number of photons which would pass through the pipe during the sampling period if the pipe were empty.

The above mentioned ratio makes it possible to determine the beam attenuation and, thus, to obtain the fluid density.

The above indicated calculation of density is affected by uncertainty, due to the fact that the photon emission from the source is a random phenomenon, subject to the known statistical Poisson distribution.

Accordingly, the number of photons emitted by the source during a sampling period of given length varies randomly, irrespective of the actual density of the fluid.

It is known that, for a Poisson statistical distribution, the uncertainty decreases as the number of counts per sample increases, i.e. as the source intensity and/or the length of the sampling period increase.

For example, in order to obtain a measurement of the signal with an uncertainty lower than 2% for at least 95% of the measurements, it is necessary to count at least 10000 photons per sample.

In fact, a 95% confidence corresponds to an uncertainty equal to twice the standard deviation of the sample size, i.e. the number of counts per sample, divided by the size itself, where the standard deviation (usually indicated as "sigma") is the square root of the size of the sample.

Usually, in the oil production field, a sample size in the order of 100000 counts is used to obtain a measure with a small enough uncertainty.

Nevertheless, the maximum intensity of the radioactive source in a densitometer is limited due to the restrictions concerning the safety and the overall dimensions of the instrument, which in turn limit the average number of photons emitted by the source in the time unit.

Therefore, in order to obtain samples with the above mentioned size, it is necessary to use sampling periods with lengths in the order of one second.

Nevertheless, such sampling times are too long to allow for the detection of density changes due to the discontinuous gas flow through the pipe, because these changes occur in time intervals that are much shorter than one second.

Therefore, the aforementioned known technique poses the drawback of not being fast enough to allow the quick changes in the gas fraction to be measured with enough accuracy, only allowing average density measurements.

The above mentioned drawback increases the uncertainty regarding the density measurements, particularly for multiphase fluids in the oil production field.

In fact, since the oil fraction is related to the input values, i.e. the measured density and the electrical properties, through a highly non-linear correlation, the averaging of the input values causes a degradation of the result.

Moreover, since water and oil have much higher densities than gas, the overall density of such fluids decreases as the gas fraction increases, and the uncertainty of the density measurement become more relevant, in percentage, compared to the measured value.

Therefore, when the fluid flow is affected by quick changes in the gas content, the above described known technique is unable to give accurate density measurements, since these measurements also take into account the high gas content periods which, as just mentioned, cause high uncertainty in the measurements.

Since the water and oil densities are very similar, said uncertainty strongly affects the calculation of the water-cut and therefore the calculation of the oil fraction, causing the drawback of producing highly unreliable measurements.

Figure 6:
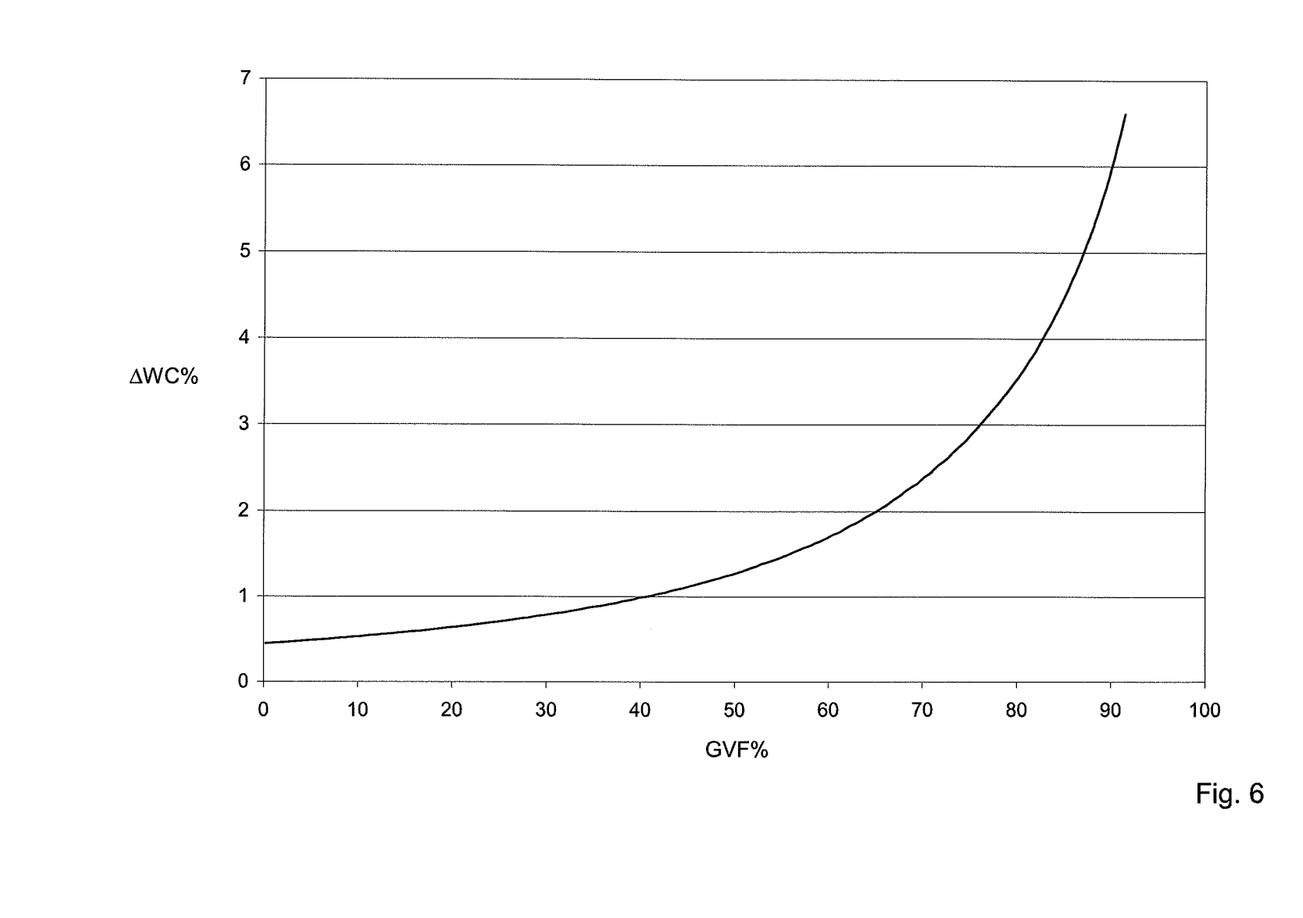
FIG. 6 shows diagrammatically the uncertainty in the water-cut measurement as a function of the gas volume fraction in a multiphase fluid.

What is described above is apparent from the diagram of FIG. 6, which expresses the uncertainty in the water-cut (ΔWC %) vs, the gas volume fraction in the fluid (GVF %), assuming the density measurement be affected by a 2% error.

In the attempt to remedy the above mentioned drawbacks at least partly, a further technique has been developed, which is described in the International Patent application WO2008150180 A2 by ROXAR FLOW MEASUREMENT AS.

According to this technique, the samples for the density measurement are collected during the low gas content periods only, while the photons detected during the high gas content periods are discarded.

This technique ensures, at least in theory, more reliable density measurements than the previous one since the density measurement corresponding to low gas content periods is affected by a lower degree of uncertainty.

The low gas content periods are detected through the measurement of an electric property of the fluid.

The above mentioned electric property measurement is much quicker than the density measurement, thus allowing to follow the instantaneous changes in the gas flow rate.

Despite allowing the uncertainty related to the presence of gas in the fluid to be reduced, the above technique nevertheless poses the drawback of noticeably increasing the duration of each density measurement.

In fact, since the photons corresponding to high gas content periods are discarded from the density measurement, it is necessary to extend the sampling period to several consecutive low gas content periods to obtain the predetermined number for each sample.

Nevertheless, these consecutive periods are distributed over an overall time period which is much longer than the actual length of the periods themselves.

Therefore, this technique doesn't allow the instantaneous monitoring of the water-cut, hence causing uncertainty when determining the oil fraction in the multiphase fluid.

BRIEF SUMMARY OF THE INVENTION

The present invention aims at overcoming all of the above mentioned drawbacks of the prior art.

In particular, it is a first object of the invention to provide a densitometer that makes it possible to determine the density of a liquid mixture flowing through a pipe in a quicker and more accurate manner compared to the known technique.

In particular, it is an object of the invention to make it possible to determine the density of the mixture substantially instantaneously, even when a gas flows through the pipe with discontinuous flow rate.

A further object of the invention is to provide a densitometer that fulfils the requirements concerning safety and dimensions relating to the oil production field.

It is also an object of the invention to provide a multiphase meter with a higher accuracy than the known ones.

The aforesaid objects are achieved by a method for determining the density according to claim 1.

The said objects are also achieved by a densitometer according to claim 12, as
well as by a multiphase meter according to claim 22.

Further details of the method and the densitometer of the invention are specified in the corresponding dependent claims.

Advantageously, the faster measurement permitted by the invention makes it possible to detect the changes in the fluid density due to the discontinuous gas flowing through the pipe which, as above mentioned, are very fast.

Therefore, advantageously, the instantaneous density measurement may be combined with the measurement of an electrical property of the fluid, for example conductivity or dielectric permittivity, thus making it possible to determine the instantaneous gas fraction and water-cut.

Advantageously, the above mentioned instantaneous measurements avoid the use of averaging input values to calculate the parameters of the fluid, thus avoiding the above mentioned measurement errors deriving therefrom.

This makes it possible to obtain an oil fraction measurement which is more reliable compared to the prior art.

BRIEF DESCRIPTION OF THE DRAWINGS

The said objects and advantages, and others which are better highlighted below, will be illustrated in detail in the description of a preferred embodiment of the invention which is provided by way of non-limiting example with reference to the attached drawings, wherein.

DETAILED DESCRIPTION OF THE INVENTION

Figure 1:
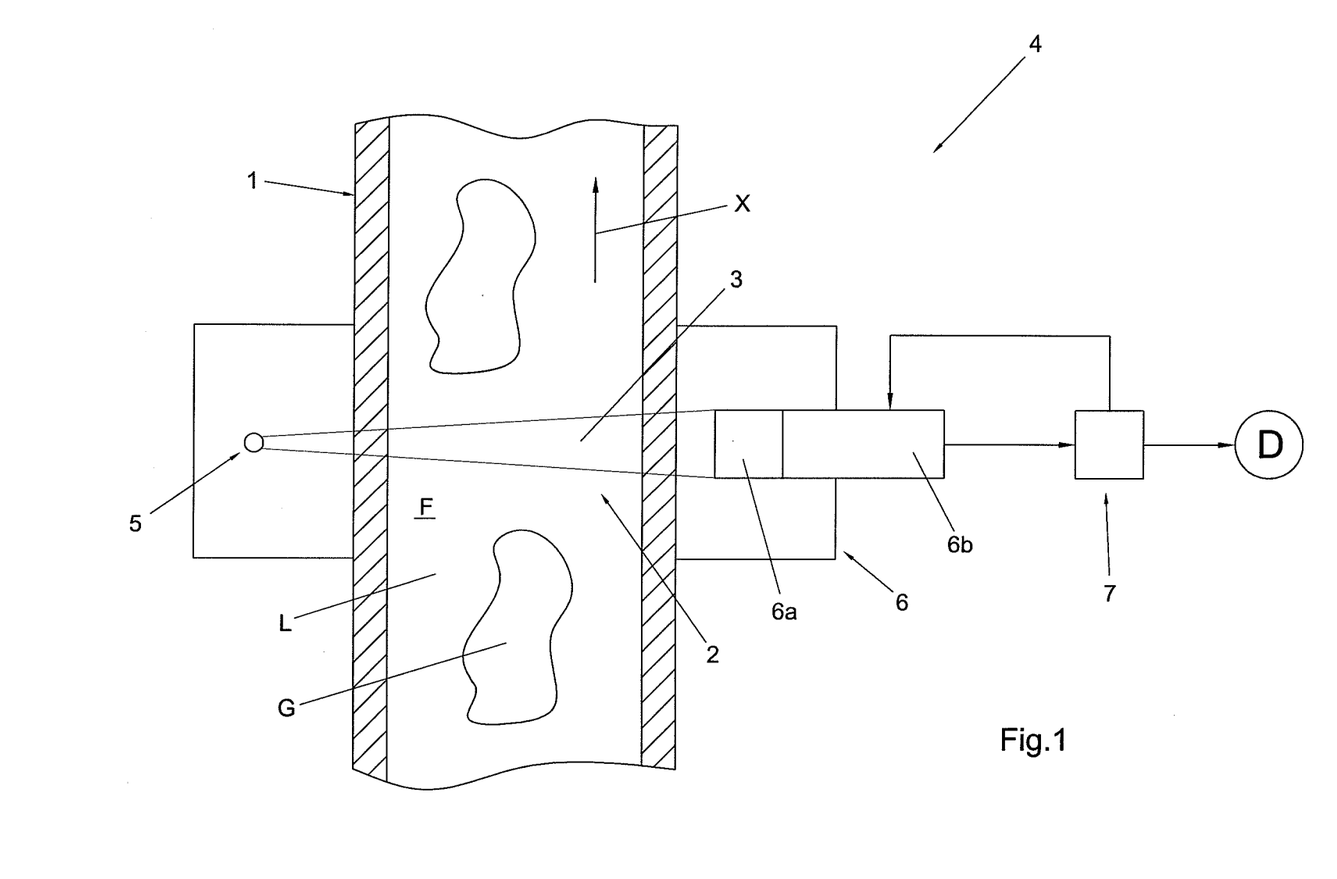
FIG. 1 shows a schematic view of the densitometer that is the subject of the invention.

As previously explained and schematically illustrated in FIG. 1, the method of the invention makes it possible to determine the density D of a multiphase fluid F comprising a liquid phase L and a gas G which flows in a pipe 1, in relation to each one of a series of consecutive time periods, i.e. the "sampling periods", in particular when the multiphase fluid F is an oil/water/gas mixture produced from an oil-well.

Figures 3, 4:
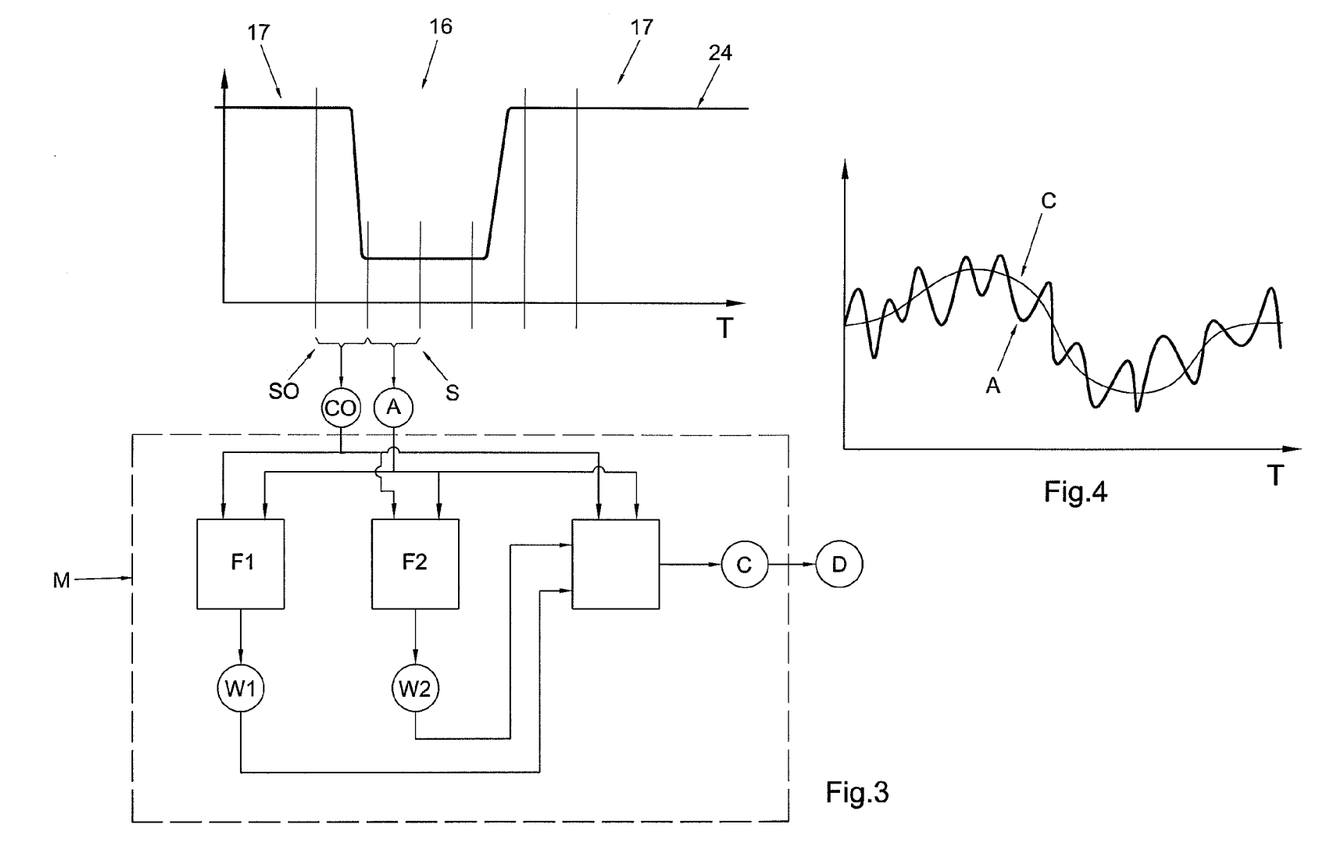
FIG. 3 shows a step of the method that is the subject of the invention.
FIG. 4 shows the trend of some values calculated with the method that is the subject of the invention.

This method is particularly useful when the flow of the gas G is discontinuous, as shown schematically by the curve 24 of FIG. 3, indicating in the Y-axis the quantity of gas at the level of a section 2 as a function of time T, indicated in the X-axis.

The above mentioned discontinuous flow determines a time fluctuation on the actual instantaneous density of the fluid F, whose frequency-components are characteristic of the type of oil/water/gas mixture flow occurring in the pipe 1.

For the sake of simplicity, the method of the invention is described making reference to a densitometer 4 schematically illustrated in FIG. 1 and comprising a radioactive source 5 configured so as to emit a photon beam 3 and to convey it through a section 2 of the pipe 1.

The photon beam 3 is suited to undergo an attenuation that depends on the density of the fluid F which the photon beam 3 crosses.

A fraction of the photons that emerge from the opposite side of the pipe 1 are intercepted by a transducer 6 that emits an electric signal corresponding to each intercepted photon.

The interception of photons and the emission of the corresponding electric signals is preferably carried out by means of a scintillator 6a of a known type, having a high detection efficiency at the energy of the photons used for the measurement.

The scintillator 6a is coupled with a signal amplifier 6b with variable gain which preferably comprises a photomultiplier of known type.

The densitometer 4 also comprises a logic processing unit 7 configured so as to count the number of signals emitted by the transducer 6 during a first time period S of predetermined length, in order to obtain a corresponding actual count A.

It is evident that the reference to a first time period S given above is meant to identify any specific time period among the series, and not the first one occurring in time.

The logic processing unit 7 is also configured for implementing a predefined algorithm M which converts the value of the above mentioned actual count A into the density D of the fluid F, as schematically shown in FIG. 3.

According to the invention, the sampling frequency, defined as the number of time periods per second, is set to be higher than the highest of the above mentioned frequency-components of the density fluctuation occurring in the flowing fluid F due to the discontinuous flow rate of the gas G.

The said highest frequency can be estimated in a known way, because it is characteristic of the type of oil/water/gas mixture flow under consideration.

The above mentioned reduction of the time periods S, which is contrary to the teaching derivable from the previously mentioned known technique, makes it possible to obtain a measurement of density D which, practically, corresponds to an instantaneous measurement.

According to the invention, the predefined algorithm M also implements an iterative technique for filtering the value of the actual count A by using the counts corresponding to the time periods preceding the above mentioned first time period S, so as to reduce the statistical variability of the measurement within a value that is compatible with the required accuracy.

Specifically, the predefined algorithm M calculates a corrected count C for said first time period S as a weighted average between the actual count A, multiplied by a first weighting factor W1, and the corrected count calculated during the time period S0 which precedes the first time period 5, which will be called previous corrected count C0, multiplied by a second weighting factor W2, according to the following formula:

$$C = A \times W1 + C0 \times W2.$$

The predefined algorithm M then converts the corrected count C into a corresponding value of density D through a predefined function which can be of a type similar to those already known and which takes into account the ratio between the corrected count C and the count that would theoretically be obtained if the pipe 1 were empty, as the density of the fluid F depends on said ratio.

This formulation is different from that applied in the methods of known type above mentioned, where in fact the density D is obtained only based on the actual count A collected during the first time period S.

The effect of the correction described above is schematically illustrated in FIG. 4, where it can be observed that the curve of the corrected count C doesn't present oscillations due to the statistical variations which on the other hand inevitably affect the curve of the actual count A.

Therefore, the combination of short time periods S with the correction described above makes it possible to obtain a value of the density D corresponding to each single time period, thus with high frequency, and with an accuracy that is higher than that obtained with the known methods mentioned above, thus achieving one of the objects of the invention.

Advantageously, the higher frequency of the measurement makes it possible to avoid the measurement errors typical of the known methods that employ longer time periods for the sampling.

Still advantageously, the method of the invention makes it possible to increase the frequency of the measurement with no need to considerably increase the intensity of the photon source 5 compared to the known methods.

Therefore, the invention achieves the object to use a source 5 whose intensity and overall dimensions are compatible with the known uses, in particular with the use in the oil production industry.

As already explained, the predefined length of the time periods is chosen according to the highest frequency-component in the flow, which depends mainly on the type of oil-well.

In the case of a multiphase fluid extracted from an oil-well, the highest frequency-component is of the order of 50 Hz.

Therefore, in this case, a suitable predefined length for the time periods is shorter than 1/50 s and, preferably, 1/125 s.

With such a predefined length, the time periods are also shorter than the shortest low gas content periods, i.e. the periods during which the gas G occupies a relatively small percentage of the section 2, one of which is indicated in the curve of FIG. 3 with the reference 16 and that, normally, is in the order of 1/50 s.

Therefore, some density measurements fall entirely within the low gas content periods, allowing for a reduced uncertainty in the calculation of GVF and water cut, as already explained during the above description of the known art.

Furthermore advantageously, such a higher frequency of measurement allows the low gas content periods 16 to be distinguished from the high gas content periods 17 directly through the density measurement, with no need to measure other values, like for example an electric property.

However it is evident that, in embodiments of the invention used in flows of different type with respect to the one above mentioned, the predefined length can be different than that above indicated, even longer than 1/50 s, provided it is comparable to the highest frequency-component in the flowing mixture.

Preferably, with reference to FIG. 3, the weighting factors W1 and W2 are calculated by means of corresponding functions F1 and F2 detailed hereinafter, on the basis of the values of the actual count A, of the previous corrected count C0, and of a parameter Q0 which represents the statistical certainty of the previous corrected count C0.

Regarding the first weighting factor W1, it is preferably calculated in two steps. The first step is a so-called time update step, in which:
1) a correction factor W0 is calculated as the squared difference between the actual count A and the previous corrected count C0, divided by the previous corrected count C0;
2) an intermediate uncertainty $Q_{int}$ is estimated for the corrected count C, by adding to the value of said uncertainty parameter Q0 an amount equal to the correction factor W0 multiplied by a scale coefficient P.

In mathematical terms:

$$W0 = (A - C0)^2 / C0$$

and $$Q_{int} = Q0 + P \times W0.$$

In statistical terms, the above mentioned correction factor W0 represents the ratio between the squared deviation of the actual count A in relation to the previous corrected count C0 and the previous corrected count C0, which represents the variance of the sample.

The ratio to the variance makes it possible to normalise the quadratic deviation, thus allowing it to be expressed in statistical terms.

Statistically, the correction factor W0 is a measure of the probability that the deviation of the actual count A from the previous corrected count C0 is due to a real fluctuation in the density D, or lies within the expected statistical fluctuations of the measurement of the actual count A which occur even when the density D is constant.

If the correction factor W0 is less than 1, there is a greater than 60% probability that the deviation is predominantly a statistical fluctuation in the measurement of the actual count A.

When the correction factor W0 is 2 or more, there is a 95% probability that the deviation is predominantly caused by a real change in the density D.

The correction factor W0 is calculated from terms which must always be positive, so:

$$Q > Q0 > 0.$$

In statistical terms, the time update step just described is a prediction step, in which it is predicted that the new value of the corrected count C will be the same as the previous corrected count C0.

The increase in the intermediate uncertainty $Q_{int}$ represents the increase in the uncertainty of this estimate of the corrected count C, implied by the deviation of the actual count A from the previous corrected count C0.

The above formulas show that the more the actual count A deviates from the previous corrected count C0, the greater is the resulting increase in the intermediate uncertainty $Q_{int}$.

The second step for the calculation of the weighting factor W1 is made by using the above mentioned function F1, expressed by the next formula:

$$W1 = F1(A, C0, Q0) = Q_{int}/(Q_{int} + C0).$$

In this way, the correction factor W0 exerts its influence on the calculation of the value of the first weighting factor W1, which, because the intermediate uncertainty $Q_{int}$ and the previous corrected count C0 are always higher than 0, must always lie in the range 0<W1<1.

This method of calculation takes in consideration the fact that the higher is the variation in the actual count A compared to the previous corrected count C0, the higher is the probability that this variation is due to an actual fluctuation in the density of the fluid F.

In particular, as the correction factor W0 increases with the square of the deviation, if the square of this deviation is significantly greater than the previous corrected count C0, the value of the intermediate uncertainty $Q_{int}$ very quickly becomes greater than the previous corrected count C0, causing the value of the first weighting factor W1 to approach 1.

As a consequence, the calculated value for the density D quickly approaches the actual value of the actual density of the fluid, even if the latter changes rapidly.

Consequently, the calculation algorithm described above has a high response speed and therefore makes it possible to identify also the quick variations due to the discontinuous flow of the gas G.

On the contrary, the lower is the deviation of the actual count A compared to the previous count C0, the higher is the probability that this deviation is due to the statistical noise of the measurement of the actual count A.

In this case, the fact that the correction factor W0 depends on the square of the deviation causes the actual count A to affect the calculation of the density D only slightly, thus advantageously making it possible to reduce the influence of the statistical noise and thus increasing the reliability of the calculation of the density D.

As regards the scale coefficient P, its value can be chosen based on the characteristics of the motion of the fluid and on the response speed desired for the filter.

In particular, a higher value of the scale coefficient P determines a higher response speed, while a lower value determines a higher stability of the filter.

In the case of oil-wells, it has been observed that a value of the scale coefficient P included between 0.005 and 0.3 makes it possible to reach a good compromise between the two aspects described above.

As regards the second weighting factor W2, it is preferably obtained by subtracting said first weighting factor W1 from 1 using the following function F2:

$$W2 = F2(A, C0, Q0) = 1 - W1.$$

Finally, a new parameter Q representative of the statistical uncertainty of the corrected count C is calculated using the following function F3:

$$Q = F3(A, C0, Q0) = W2 \times Q_{int}.$$

In the time period subsequent the first time period S, the density D will be calculated again in the same way as explained above, detecting a new actual count A and using the new uncertainty parameter Q and the corrected count C respectively as uncertainty parameter Q0 and previous corrected count C0.

Figure 2:
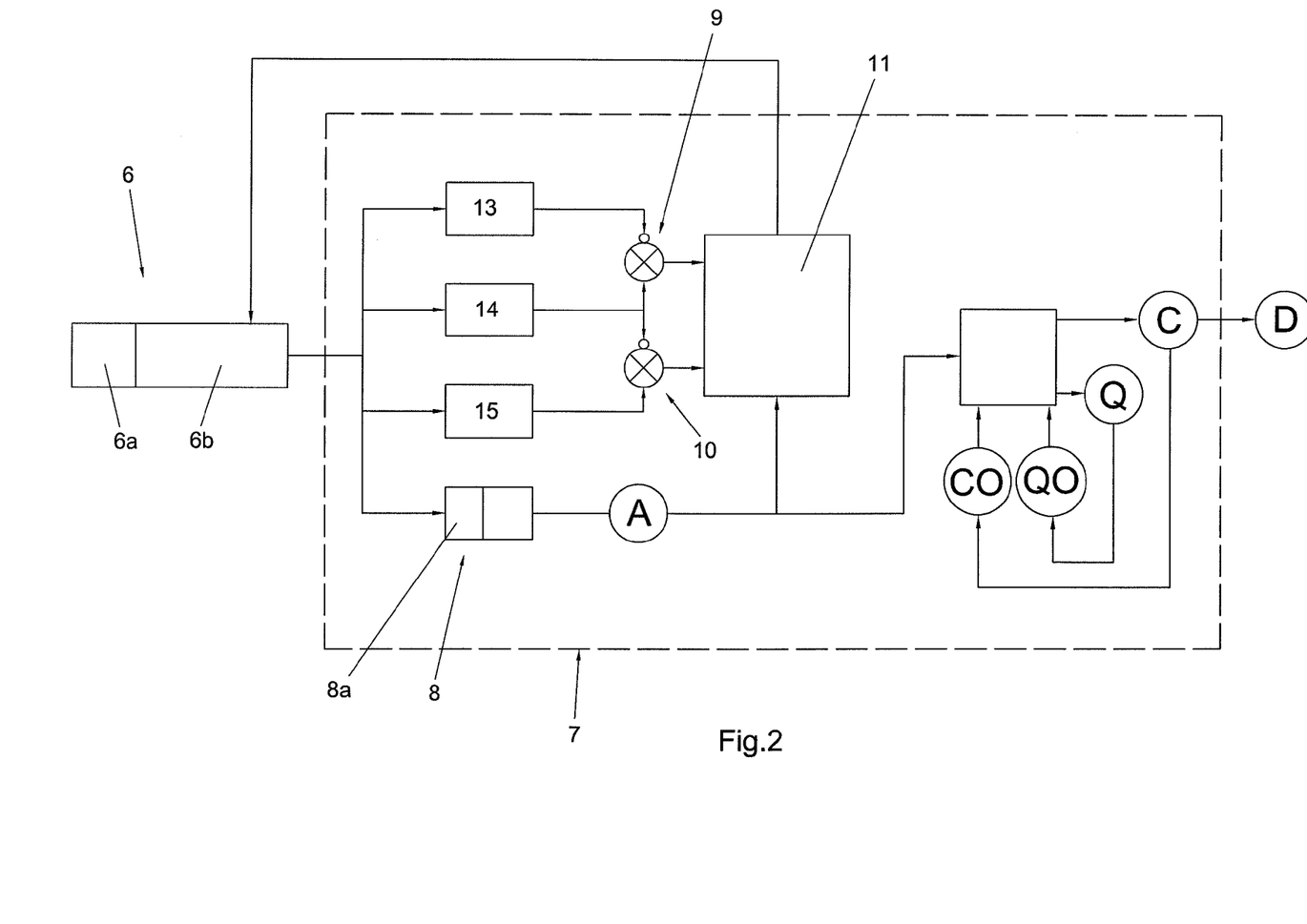
FIG. 2 shows a detail of the photon detection system of the densitometer of FIG. 1.

In order to allow using the corrected count C and the new uncertainty parameter Q for the subsequent time period, they are stored by the logic processing unit 7, as schematically shown in FIG. 2.

As regards the calculation of the corrected count C corresponding to the initial time period of the series, as there is neither a previous corrected count C0 nor a previous estimated uncertainty Q0, these are replaced by corresponding predefined initial values.

Preferably, these predefined initial values are both set equal to the actual count A corresponding to that measured in the said initial time period.

An expert may notice that the calculations above as a whole fall within a formulation of an adaptive Kalman filter for a single variable process.

As is known, Kalman filters are special time varying statistical filters that make it possible to estimate the state of a process subjected to random disturbances from a noisy measurement of said state.

It is also known that a Kalman filter represents an optimal filter, in the least squares sense, provided the disturbances of the process and the measurement noise are independent of each other and both randomly changing according to corresponding gaussian distributions.

In practice, the above mentioned conditions occur in the present invention during the periods when the fluid is mostly liquid or mostly gaseous, where the disturbances due respectively to the flow of small bubbles in the liquid flow or small droplets in the gas flow are found to produce density fluctuations having an approximately gaussian distribution.

As to the measurement, it corresponds to the counts of the photons emitted by the source 5 during the time periods, and it is governed by a Poisson distribution.

Considering the high number of counts of each sample, the Poisson distribution practically corresponds to a Gaussian distribution.

Therefore, advantageously, the said Kalman filter, when used in the density measurement of a flow of the kind described above, is approximately the optimal filter in the least squares sense.

Regarding the counting of the actual number A of photons, this comprises the step of intercepting the photons of the attenuated beam 3 by means of the transducer 6.

For each one of the above mentioned photons that is intercepted, the transducer 6 emits a corresponding signal that is successively amplified by the amplifier 6b according to the corresponding gain factor.

The amplified signals emitted during the first time period S are counted by a counter 8 belonging to the logic processing unit 7 that determines the actual count A.

Figure 5:
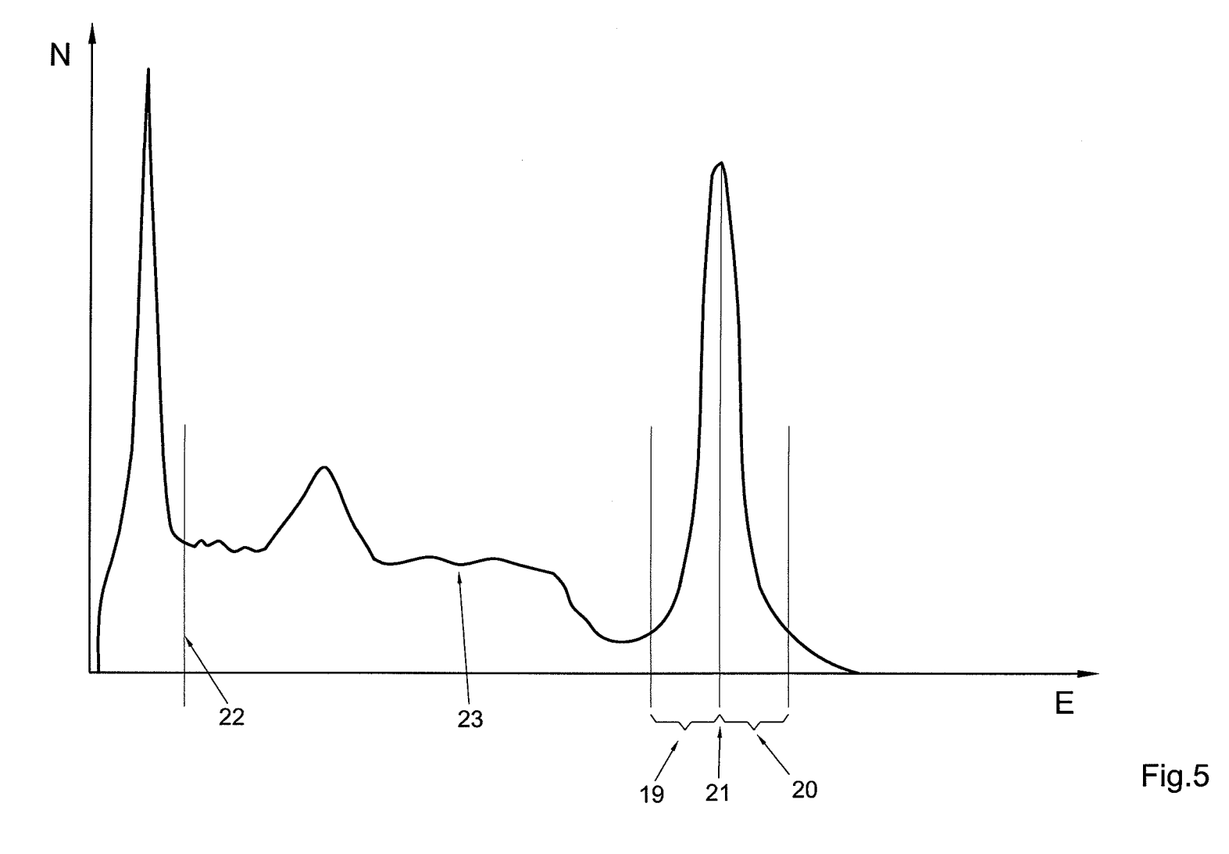
FIG. 5 shows a typical spectrum for the energy given up to a scintillator by the detected gamma photons.

By considering the number N of signals produced by the photons intercepted by the transducer 6 as a function of their energy E, it is possible to obtain a spectrum that is similar to that shown in FIG. 5, whose shape depends only on the source 5 and the transducer 6.

Generally, the shape of the spectrum is determined by the physics of the way the detected photons interact with the scintillator.

In particular, the spectrum of FIG. 5 is obtained by employing a 137 Cs source coupled with a transducer made of LaBr3.

Obviously, it is possible to use sources and transducers that are different from those indicated above, thus obtaining a spectrum with a shape different from the one represented herein.

As will be described below, the spectrum may vary in detail due to the influence of some external parameters but, anyway, these variations do not alter the fundamental geometrical proportions of the spectrum, hence they do not alter its form.

In particular, the existence of a relatively narrow photopeak at the high energy tail of the spectrum, with a trough followed by a more or less uniform distribution of counts in the Compton continuum below this, is preserved.

Whatever the spectrum obtained, it also comprises a certain number of "noisy" signals that do not correspond to intercepted photons, but to the background noise of the transducer 6.

In particular, the above mentioned spurious signals are arranged in the low energy part of the spectrum and may affect the count of the signals actually corresponding to the intercepted photons.

Therefore, the method of the invention preferably excludes from the actual count A the amplified signals with energy below a predetermined threshold level 22, which represents the maximum energy level of the signals due to the background noise of the transducer 6.

Advantageously, the above mentioned exclusion eliminates the disturbances due to the background noise from the count, thus making it possible to increase the accuracy of the count and therefore of the calculated density D.

In practice, the exclusion described above is preferably carried out by means of a comparator 8a belonging to the above mentioned counter 8, which eliminates the signals whose energy is below said threshold level 22.

According to a further aspect of the method of the invention, preferably the counting operation includes a first count of the amplified signals with energy included within a first predefined interval 19 and a second count of the amplified signals with energy included within a second predefined interval 20.

The two counts mentioned above are obtained by means of corresponding auxiliary counters 9 and 10 belonging to the logic processing unit 7, illustrated in FIG. 2.

The logic processing unit 7 also comprises a stabilizer device 11, interposed between the transducer 6 and the auxiliary counters 9 and 10.

The above mentioned stabilizer device is configured in such a way as to modify the gain factor of the amplifier 6b in order to maintain the ratio between the counts of the two auxiliary counters 9 and 10 within a prefixed range, so as to produce a feedback effect on the amplifier.

Advantageously, when the above mentioned threshold level 22 is used, the double count and the modification of the gain factor described above make it possible to avoid calculation errors due to a possible drift of the spectrum along the axis of energy E.

More precisely, the energy of the signals produced by the transducer 6 does not depend only on the ways in which the photons interact with the transducer 6, but also on other parameters external to the measurement apparatus, in particular on the temperature and age of the transducer 6.

The above mentioned external parameters, though not affecting the overall photon count, alter the energy value of the signals emitted by the transducer 6, causing a corresponding compression or expansion of the spectrum along the axis of energy E.

This shift alters the effect of the threshold level 22 and thus affects the accuracy of the calculation, since it modifies the percentage of signals due to the background noise compared to the signals due to the intercepted photons.

As the above mentioned shift modifies also the ratio between the number of signals included within the energy intervals 19 and 20, the above mentioned ratio allows to detect the shift and to correct it modifying the gain factor, so as to compensate for the shift and bring the spectrum back to its initial configuration.

Therefore, advantageously, the double count and the modification of the gain factor make it possible to produce a densitometer that is stable over time and does not need to be set repeatedly by field technicians.

The intervals 19 and 20 are preferably defined by means of three comparators 13, 14 and 15, operatively connected to the auxiliary counters 9 and 10, as shown in FIG. 2.

Each one of the comparators 13, 14 and 15 allows the passage of the signals with energy above one of the energy thresholds that delimit the predefined intervals 19 and 20.

In particular, the first auxiliary counter 9 calculates the first count through the difference between the signals coming from a second comparator 14 having a threshold equal to the upper limit of the first predefined interval 19, and the signals coming from a first comparator 13 having a threshold equal to the lower limit of the first predefined interval 19.

Analogously, the second auxiliary counter 10 calculates the second count through the difference between the signals coming from a third comparator 15 having a threshold equal to the upper limit of the second predefined interval 20 and the signals coming from the second comparator 14.

The comparators 13, 14 and 15 described above define two energy intervals 19 and 20 adjacent to each other, as shown in FIG. 5.

In particular, the upper limit of the first predefined interval 19 and the lower limit of the second predefined interval 20 are both equal to one common energy value 21, which is the threshold level of the second comparator 14.

The above mentioned common value 21 is preferably equal to an emission peak which is characteristic of the specific source used.

In particular, the common value 21 is equal to the emission peak corresponding to the energy of the photons emitted by the source 5 that, in the case of a source of 137 Cs, is equal to 662 keV.

Obviously, in different embodiments of the invention it is possible to use a common value 21 different from the one indicated above, in particular in the case where different source-transducer pairs are used.

In further embodiments of the invention, the two predefined intervals 19 and 20 can also be separated from each other, for example by using four comparators instead of the three described above, connected in pairs to a corresponding counter of the auxiliary counters 9 and 10.

As already mentioned, the source 5 is preferably 137 Cs which, advantageously, emits photons with sufficient energy to pass through the thickness of the steel commonly used for making oil pipes, in the order of 20 mm.

Preferably, the intensity of the source 5 is comprised between 10 mCi and 250 mCi, with a preferred value of about 100 mCi, corresponding to an average emission frequency of approximately three million photons per second within the measurement cone.

Considering the attenuation due to the material of the pipe 1 and the efficiency of the transducer 6, the photons intercepted by the transducer 6 are reduced to approximately 0.5-2 million per second.

Preferably, but not exclusively, the scintillator 6a of the transducer 6 is based on a LaBr3 crystal that is advantageously suited to intercept the above mentioned number of photons and to emit a single signal corresponding to each photon intercepted, which has a sufficiently short decay time to avoid "pile-up" phenomena that would cause measurement errors.

Using a sampling frequency of 125 samples per second, corresponding to time periods of 8 ms duration each, the above mentioned quantity of photons makes it possible to obtain samples of 4000-16000 counts each.

Using the known techniques, the number of counts indicated above would make it possible to reach a measurement uncertainty of approximately 6% with a confidence of 95%.

Using the adaptive Kalman filter according to the invention, the above mentioned uncertainty is reduced to approximately 2%.

Obviously, in further embodiments of the invention it is possible to use sources and transducers of a type different from those described above, preferably suited to obtain higher emission and calculation frequencies.

For example, for the scintillator 6a, instead of a LaBr3 crystal it is possible to use a CsF crystal or another material capable of detecting the photons with the same speed.

Similarly, the source 5 may contain a radioactive element different from 137 Cs, provided that it is capable of emitting an equivalent photon beam with a photon energy high enough to allow the photons to pass through the pipe 1.

The above shows that the measurement method and the densitometer of the invention achieve all the set objects.

In particular, the use of a short time period combined with the correction of the count through the filtering operation described above makes it possible to obtain more frequent and accurate density measurements compared to the known techniques.

Consequently, it is possible to make substantially instantaneous density measurements for a multiphase fluid comprising a gas that flows with discontinuous flow rate.

Furthermore, the invention makes it possible to obtain the above mentioned results using radioactive sources whose intensity is substantially equivalent to that of the sources commonly used in the known art.

In any case, further changes neither described herein nor illustrated in the drawings must all be considered protected by the present patent provided they fall within the scope of the following claims.

The invention claimed is:

1. Method for determining the density of a multiphase fluid flowing through a pipe in relation to each time period of a series of consecutive time periods, when said multiphase fluid contains a gas being subject to a discontinuous flow which determines a fluctuation of the actual instantaneous density of said multiphase fluid, said method being particularly suited for multiphase fluids produced m oil-wells, comprising the following steps:
   a) conveying through a section of said pipe a photon beam suited to undergo an attenuation depending on the density of the fluid being crossed by said photon beam;
   b) counting the actual number of photons of said beam which cross said pipe during a current time period of said series to define a corresponding actual count;
   c) determining the density of said multiphase fluid corresponding to said current time period according to the value of said actual count through a predefined algorithm;
   d) repeating steps b) and c) for each subsequent time period in said series of consecutive time periods;
   wherein said method comprises the following steps:
      establishing the highest frequency-component of said fluctuation of the actual instantaneous density, characteristic of said discontinuous flow of said gas;
      defining a time length for said time periods such that said time periods are shorter than the time length corresponding to said highest frequency;
   wherein said predefined algorithm comprises the following steps:
      calculating a corrected count as the weighted average value of said actual count for the current time period, multiplied by a first weighting factor, and of the previous corrected count calculated for the time period preceding the current time period in said series of consecutive time periods, multiplied by a second weighting factor;
      converting the value of said corrected count into a corresponding value of said density through a predefined function.

2. Method according to claim 1) wherein said predefined time length for said time periods is shorter than 1/50 second.

3. Method according to claim 1) wherein said first weighting factor is calculated through the following steps:
   providing a parameter representative of the statistical uncertainty of said previous corrected count;
   calculating a correction factor as the squared difference between said actual count and said previous corrected count, divided by said previous corrected count;
   calculating an intermediate uncertainty as the sum of said uncertainty parameter and of said correction factor multiplied by a scale coefficient;
   calculating said first weighting factor by dividing said intermediate uncertainty by the sum of said intermediate uncertainty and of said previous corrected count.

4. Method according to claim 3) wherein said second weighting factor is calculated by subtracting said first weighting factor from 1.

5. Method according to claim 4), further comprising the following steps:

calculating a new parameter representative of the statistical uncertainty of said corrected count by multiplying said intermediate uncertainty by said second weighting factor;

using said new uncertainty parameter and said corrected count respectively as the uncertainty parameter and as the previous corrected count for determining the density corresponding to the time period subsequent to the current time period in said series of consecutive time periods.

6. Method according to claim 3), further comprising an initialisation step for setting the uncertainty parameter and the previous corrected count corresponding to an initial time period of said series to respective predefined values.

7. Method according to claim 6) wherein said predefined values are equal to the value of the actual count detected during said initial time period.

8. Method according to claim 1) wherein the counting of said actual number of photons comprises the following steps:

intercepting the photons of said attenuated beam;
emitting a signal for each one of said intercepted photons;
amplifying said signal according to a predetermined gain factor;
counting the signals emitted during the current time period.

9. Method according to claim 8) wherein said amplified signals having an energy lower than a predetermined threshold level are excluded from said actual count.

10. Method according to claim 9), further comprising the step of adjusting said gain factor such that the ratio between the number of said amplified signals whose energy is comprised within a first predefined interval and the number of said amplified signals whose energy is comprised within a second predefined interval is maintained within a prefixed range.

11. Method according to claim 1) wherein said fluid is a mixture of water, oil and gas extracted from an oil-well.

12. Densitometer for determining the density of a multiphase fluid flowing through a pipe in relation to each time period of a series of consecutive time periods, when said multiphase fluid contains a gas being subject to a discontinuous flow which determines a fluctuation of the actual instantaneous density of said multiphase fluid, said densitometer comprising:

a radioactive source, configured to convey through a section of said pipe a photon beam suited to undergo an attenuation depending on the density of the fluid being crossed by said photon beam;

a transducer configured to intercept the photons of said photon beam that cross said pipe and to emit a signal corresponding to each one of said intercepted photons;

a logic processing unit configured for counting the actual number of signals emitted by said transducer during each time period of said series, and for calculating said density of said fluid in relation to each time period according to the value of said actual number;

wherein said logic processing unit is configured for calculating said density through a method according to claim 1).

13. Densitometer according to claim 12) wherein said source is 137Cs.

14. Densitometer according to claim 13) wherein said source has an intensity comprised between 10 mCi and 250 mCi.

15. Densitometer according to claim 12) wherein said transducer comprises a scintillator.

16. Densitometer according to claim 15) wherein said scintillator comprises an LaBr3 crystal.

17. Densitometer according to claim 12) wherein said transducer comprises a signal amplifier having a variable gain.

18. Densitometer according to claim 17) wherein said amplifier comprises a photomultiplier.

19. Densitometer according to claim 17) wherein said logic processing unit comprises a comparator configured for detecting the signals having an energy lower than a predetermined threshold value.

20. Densitometer according to claim 19) wherein said logic processing unit comprises a first auxiliary counter configured for counting the signals whose energy is comprised within a first predefined interval and a second auxiliary counter configured for counting the signals whose energy is comprised within a second predefined interval.

21. Densitometer according to claim 20) wherein said logic processing unit comprises a stabilizer device, operatively connected to said transducer and to said auxiliary counters and configured to change said gain so as to maintain the ratio between the number of signals counted by said first auxiliary counter and the number of signals counted by said second auxiliary counter within a prefixed range.

22. Multiphase meter for determining the oil fraction of a mixture of water, oil and gas produced by an oil-well, comprising means for measuring an electrical property of said mixture, and
a densitometer according to claim 12).

* * * * *